US011510735B2

(12) United States Patent
Lavallee et al.

(10) Patent No.: US 11,510,735 B2
(45) Date of Patent: Nov. 29, 2022

(54) SYSTEM FOR NAVIGATING A SURGICAL INSTRUMENT

(71) Applicant: IMACTIS, La Tronche (FR)

(72) Inventors: Stephane Lavallee, Martin D'Uriage (FR); Lionel Carrat, Saint Martin D'Heres (FR); Ivan Bricault, Grenoble (FR)

(73) Assignee: IMACTIS, La Tronche (FR)

( * ) Notice: Subject to any disclaimer, the term of this patent is extended or adjusted under 35 U.S.C. 154(b) by 921 days.

(21) Appl. No.: 15/518,887

(22) PCT Filed: Oct. 19, 2015

(86) PCT No.: PCT/EP2015/074118
§ 371 (c)(1),
(2) Date: Apr. 13, 2017

(87) PCT Pub. No.: WO2016/059250
PCT Pub. Date: Apr. 21, 2016

(65) Prior Publication Data
US 2017/0224427 A1 Aug. 10, 2017

(30) Foreign Application Priority Data
Oct. 17, 2014 (EP) .................................... 14306658

(51) Int. Cl.
A61B 34/20 (2016.01)
A61B 90/00 (2016.01)
(52) U.S. Cl.
CPC .............. A61B 34/20 (2016.02); A61B 90/37 (2016.02); A61B 2034/2051 (2016.02);
(Continued)

(58) Field of Classification Search
CPC ... A61B 34/20; A61B 90/37; A61B 2090/374; A61B 2034/2051; A61B 2034/2065;
(Continued)

(56) References Cited

U.S. PATENT DOCUMENTS 6,970,585 B1* 11/2005 Dafni ..................... A61B 6/032
  128/922
7,720,522 B2* 5/2010 Solar ..................... A61B 34/20
  600/426

(Continued)

FOREIGN PATENT DOCUMENTS

EP  2 233 099 A2  9/2010
EP  2 431 003 A1  3/2012
(Continued)

OTHER PUBLICATIONS

"Rusinkiewicz; Szymon, Efficient Variants of the ICP Algorithm Aug. 2002, IEEE, pp. 145 and 150" (Year: 2002).*
(Continued)

Primary Examiner — Angela M Hoffa
(74) Attorney, Agent, or Firm — Womble Bondd Dicknson(US) LLP

(57) ABSTRACT

The invention relates to a system for navigating a surgical instrument (1), comprising a processor configured for:
obtaining a first 3D medical image of a first volume (V1) of a patient's body, said first volume (V1) comprising a reference marker (M),
registering the first 3D image with said reference marker (M),
obtaining a second 3D medical image of a second volume (V2) of the patient's body, said second volume (V2) being different from the first volume (V1) and not containing the reference marker (M) in its entirety, said first and second 3D images being obtained by a single imaging device, (Continued)

registering the second 3D medical image with the first 3D medical image, obtaining a virtual position of the surgical instrument (1) with respect to the reference marker (M) from a tracking system, determining a virtual position of the surgical instrument (1) with respect to the second 3D medical image.

34 Claims, 3 Drawing Sheets

(52) U.S. Cl.
CPC .............. *A61B 2034/2055* (2016.02); *A61B 2034/2065* (2016.02); *A61B 2034/2068* (2016.02); *A61B 2090/365* (2016.02); *A61B 2090/367* (2016.02); *A61B 2090/374* (2016.02); *A61B 2090/3762* (2016.02)

(58) Field of Classification Search
CPC .... A61B 2034/2068; A61B 2090/3966; A61B 2090/3983
See application file for complete search history.

(56) References Cited

U.S. PATENT DOCUMENTS

| | | | | |
|---|---|---|---|---|
| 2003/0220557 | A1* | 11/2003 | Cleary | A61B 5/06 600/409 |
| 2004/0042588 | A1* | 3/2004 | Janes | A61B 6/032 378/210 |
| 2004/0167391 | A1* | 8/2004 | Solar | A61B 34/20 600/411 |
| 2004/0204644 | A1* | 10/2004 | Tsougarakis | G01R 33/56 600/410 |
| 2005/0080336 | A1* | 4/2005 | Byrd | A61B 8/065 600/428 |
| 2005/0215879 | A1 | 9/2005 | Chuanggui | |
| 2006/0142657 | A1* | 6/2006 | Quaid | G06F 19/00 600/424 |
| 2006/0241432 | A1* | 10/2006 | Herline | A61B 5/06 600/437 |
| 2008/0118135 | A1* | 5/2008 | Averbuch | G06T 7/0012 382/131 |
| 2008/0188739 | A1* | 8/2008 | Rongen | A61B 6/12 600/424 |
| 2010/0172472 | A1* | 7/2010 | Ermes | A61B 6/5241 378/62 |
| 2011/0059413 | A1* | 3/2011 | Schutyser | A61B 5/1077 433/8 |
| 2011/0082363 | A1* | 4/2011 | Xu | A61B 8/4254 600/411 |
| 2011/0137156 | A1* | 6/2011 | Razzaque | A61B 18/1477 600/424 |
| 2014/0022283 | A1 | 1/2014 | Chan et al. | |

FOREIGN PATENT DOCUMENTS

| | | |
|---|---|---|
| EP | 2 233 099 A3 | 11/2014 |
| WO | WO 2010/086374 A1 | 8/2010 |

OTHER PUBLICATIONS

International Search Report and Written Opinion in PCT/EP2015/074118 dated Feb. 2, 2016.

Search Report in French Application No. 14306658.7 dated Mar. 27, 2015.

\* cited by examiner

SYSTEM FOR NAVIGATING A SURGICAL INSTRUMENT

FIELD OF THE INVENTION

The invention relates to a system for navigating a surgical instrument.

BACKGROUND OF THE INVENTION

Surgical interventions performed in interventional radiology consists of introducing a surgical instrument, such as a needle or equivalent, in the body of the patient.

The interventional radiologist uses an imaging system, most likely a Computed Tomography Scan (CT-Scan), or Cone Beam Computer Tomography (CBCT), or a Magnetic Resonance Imaging system (MRI), to see the organs of the patient and choose the target for the tip and the trajectory to be followed by the needle to reach this target. A target can be any structure of the body, such as a region of a tumour, a region of a cyst, a region of a bone, or the like.

In order to help the interventional radiologist to reach the target, a navigation system is necessary. Such navigation systems use a tracking system based on optical, electromagnetic, radiofrequency, inertial, ultrasound or mechanical technology.

The objective of the tracking system is to give the spatial position and orientation in real time of one or more trackers, one tracker having a known spatial relationship with the needle.

It is also possible to use a robot, that can be active, haptic or tele-operated and that contains a needle guide at its extremity or carry directly the needle. It can be considered that a robot is a particular case of a navigation system.

Document WO 2010/086374 describes a method for navigating a surgical instrument such as a needle in a 3D medical image of a patient. To that end, the needle is slidingly arranged in a surgical guide to which a tracker is rigidly attached, and a reference marker is attached to the patient's body and localized by the tracking system. Since the reference marker can be detected in the 3D medical image, it is possible to determine the position and orientation of the surgical guide with respect to the 3D medical image. The needle being a linear instrument, its axis is supposed to coincide with the axis of the guide. Hence, even if the needle is not itself tracked, the system allows determining the position and orientation of the needle axis in the 3D medical image.

During interventional radiology, a first 3D medical image of a region of the patient's body is acquired while the reference marker is attached to the patient's body so as to be visible on the first 3D image. However, in some cases, the reference marker is at a certain distance of the actual region of interest (e.g. a volume containing a target to be treated by the surgical instrument). This means that, in view of navigating the surgical instrument during the surgical intervention, the reference marker has to be displaced to a position closer to the region of interest, and a new 3D medical image has to be acquired. This is time consuming.

Besides, a goal of interventional radiology is to reduce the dose of X-ray absorbed by the patient when the 3D image is CT or CBCT. Said dose depends on the volume of the patient's body that is scanned in order to obtain the 3D medical image. In order to reduce the dose, one could thus consider reducing the irradiated volume.

In the case of MRI, the acquisition of the images is time-consuming. Since the acquisition time depends on the volume size, one could also consider reducing the imaged volume.

However, in order to enable navigation, this reduced volume should always comprise the reference marker in order to allow registration of the 3D medical image with data provided by the tracking system. This constraint limits the possibility to reduce the imaged volume.

In addition, if only a small volume of the patient's body is imaged, it is also more difficult for the radiologist to interpret.

BRIEF DESCRIPTION OF THE INVENTION

A goal of the invention is to allow navigating a surgical instrument with respect to a 3D medical image even if this image corresponds to a volume of the patient's body that does not comprise a reference marker in its entirety.

A further goal of the invention is to reduce the dose of X-ray applied to a patient in interventional radiology and/or to reduce the acquisition time of an image, while still allowing navigation of the surgical instrument in a 3D medical image of the patient.

To this end, an object of the invention is a system for navigating a surgical instrument, comprising a processor configured for:
- obtaining a first 3D medical image of a first volume of a patient's body, said first volume comprising a reference marker,
- registering the first 3D image with said reference marker,
- obtaining a second 3D medical image of a second volume of the patient's body, said second volume being different from the first volume and not containing the reference marker in its entirety, said first and second 3D images being obtained by a single imaging device,
- registering the second 3D medical image with the first 3D medical image,
- obtaining a virtual position of the surgical instrument with respect to the reference marker from a tracking system,
- determining a virtual position of the surgical instrument with respect to the second 3D medical image.

The system described above allows performing a method for determining a virtual position of a surgical instrument with respect to a 3D medical image, in view of navigating said surgical instrument, that comprises:
- obtaining a first 3D medical image of a first volume of a patient's body, said first volume comprising a reference marker,
- registering the first 3D image with said reference marker,
- obtaining a second 3D medical image of a second volume of the patient's body, said second volume being different from the first volume and not containing the reference marker in its entirety, said first and second 3D images being obtained by a single imaging device,
- registering the second 3D medical image with the first 3D medical image,
- obtaining a virtual position of the surgical instrument with respect to the reference marker using a tracking system,
- determining a virtual position of the surgical instrument with respect to the second 3D medical image.

According to an embodiment, the second volume is smaller than the first volume.

According to an embodiment, the first 3D image is a large volume of CT images and the second 3D medical image is a small set of CT slices of a volume of the patient's body comprising a target.

According to another embodiment, the first and second 3D images are MR images.

According to an embodiment, the surgical instrument is a needle guide.

Advantageously, a tracker is rigidly attached to the needle guide for navigation of a needle coupled to said needle guide.

According to an embodiment, the needle is detected as a trace in the second 3D medical image and the registration comprises registering said trace of the needle with the virtual position of said needle.

During said registration of the trace of the needle with the virtual position of said needle, the translation along and the rotation about the needle axis may be determined by an image to image registration technique. Preferably, said image to image registration technique is carried out in a region of interest having a known geometric relationship with the needle guide or the trace of the needle.

According to an embodiment, the second volume is included in the first volume.

Alternatively, at least a part of the second volume extends outside the first volume.

According to an embodiment, the method further comprises updating the first 3D medical image by replacing, in said first 3D medical image, the second volume by the second 3D medical image.

According to an embodiment, the registration of the first and second 3D images comprises a rigid registration based on DICOM tags of said images.

According to an embodiment, the registration of the first and second 3D images uses an image to image registration technique.

Both of said registrations may be combined such that results of the rigid registration based on DICOM tags of the images are used for initializing an iterative computation of the image to image registration technique.

Advantageously, the image to image registration technique is carried out in a region of interest having a known geometric relationship with the needle guide.

According to an embodiment, the reference marker comprises fiducials that are at least partly visible in the second 3D medical image and said image to image registration technique is carried out using said parts of the fiducials.

BRIEF DESCRIPTION OF THE DRAWINGS

Other features and advantages of the invention will be apparent from the following description, in connection with the appended drawings, wherein.

DETAILED DESCRIPTION OF EMBODIMENTS OF THE INVENTION

The general context of the method described below is a surgical intervention performed in interventional radiology, aiming at reaching a target within a patient's body with a surgical tool (such as a needle for example). The method makes use of a navigation system comprising a tracking system to track a surgical instrument which can be the tool itself or a tool guide (for example, the surgical instrument can be a needle guide if the tool is a needle).

The method can be carried out by a surgical system comprising a computer and a display device coupled to the computer to display navigation data to a user. The display device can be for example a conventional display monitor, a compact display attached to the instrument, virtual or augmented reality glasses, or the like. The computer is coupled to the navigation system to receive navigation data.

The computer comprises a processor configured to run a software to carry out the method.

A 3D medical image of a first volume of the patient's body is provided.

Said 3D medical image can be obtained for example by Computed Tomography or by Magnetic Resonance Imaging.

Said first volume comprises a reference marker that can be localized by the tracking system and that is visible on the 3D image. In a preferred embodiment, said reference marker is integrated with an electromagnetic emitter that is used as a localizer that tracks a tracker attached to the instrument.

The 3D image is registered with the reference marker, i.e. the transformation matrix between the referential system of the 3D image and the referential system of the reference marker is determined using known methods for detecting and registering fiducials in medical images. Fiducials of the reference marker can be made of many elements, such as spheres, tubes, lines, or any combinations, or the like.

Figure 6:
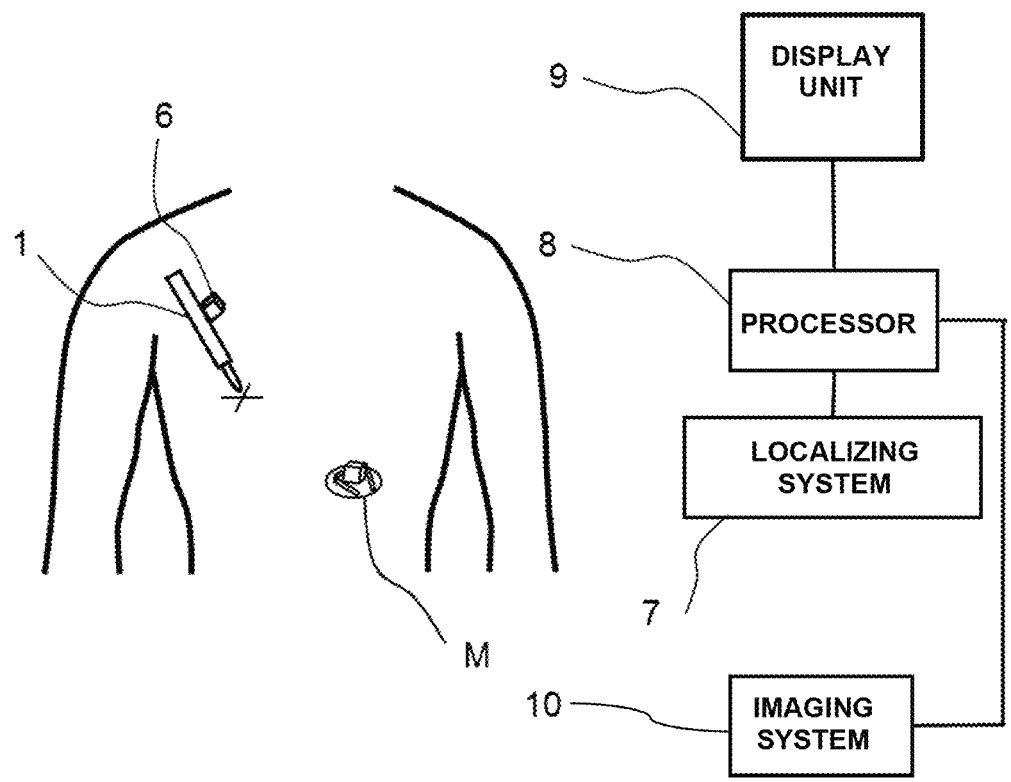
FIG. 6 schematically illustrates a navigation system according to the invention.

As shown in FIG. 6, the navigation device comprises a computer system comprising a processor 8 and a display unit 9. The navigation device further is coupled to an imaging system 10, such as a CT-scan, and comprises a localizing system 7 that includes a localizer control unit for emission and detection of magnetic field. The computer system is preferably connected to the network in order to be able to receive DICOM images from the CT workstation. A magnetic tracker 6 is fixed on the surgical instrument 1. The surgical instrument is navigated with respect to R1 using the magnetic tracker. A referential system incorporated to a marker M is provided on the patient's body in order to be in a volume corresponding to a first 3D medical image.

Figure 1:
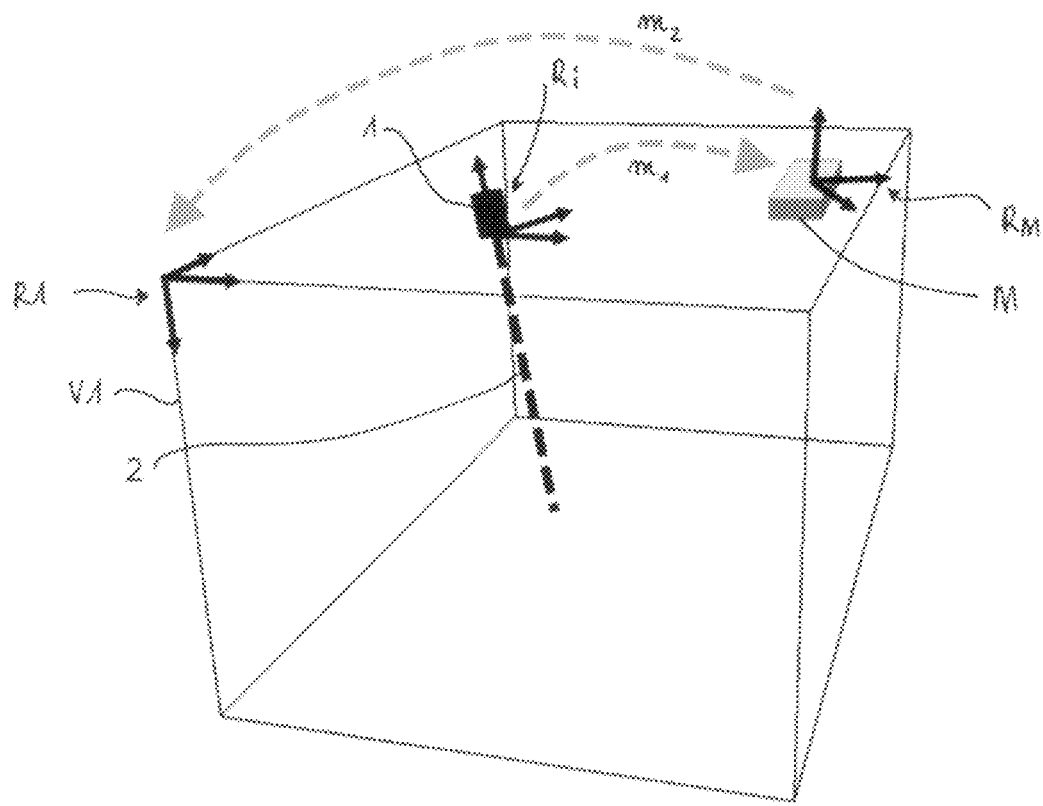
FIG. 1 illustrates the registration of the first 3D medical image with the reference marker.

FIG. 1 illustrates a 3D image of the first volume V1. A referential system R1 is attached to the 3D image. The reference marker M has a referential system $R_M$ attached thereto. In the illustrated embodiment, the surgical instrument is a needle guide 1 coupled to a needle that can slide in the needle guide 1. A referential system Ri is attached to the surgical instrument 1. The surgical instrument is equipped with a tracker (not shown) allowing the tracking system to localize the surgical instrument in real-time, with a frame rate that is generally above ten hertz. The position of the referential system Ri with respect to the referential system $R_M$ is determined by the navigation system in the form of a matrix m1. The position of the referential system $R_M$ with respect to the referential system R1 is known by a registration of the 3D image with the reference marker implemented previously (matrix m2). As a result, a virtual needle 2 can be navigated in the 3D image using a combination of matrices m1 and m2.

During a surgical intervention carried out on the patient, a second volume of the patient's body, different from the first volume, is imaged by the same 3D imaging system as the 3D imaging system that was used previously to acquire the first 3D image. Indeed, the acquisition of the first 3D image and the subsequent navigation of the surgical instrument take place during a single patient examination procedure. Hence, the reference marker remains approximately or exactly in the same position relative to the patient, depending on possible small patient motions.

The second volume is intended to navigate the surgical instrument.

In order to reduce the irradiation dose (in case of CT imaging) or the acquisition time (in case of MR imaging), the second volume is generally smaller than the first volume.

Besides, the second 3D image may not have the same resolution and/or the same orientation as the first 3D image.

For example, the first 3D image is a large volume of CT images that contains a large portion of the patient's body. Usually more than ten or twenty centimeters of images along the patient's body axis (Z direction) are acquired. And the second 3D medical image is a small set of CT slices of a volume of the patient's body comprising the region of a target to be treated by the surgical instrument. The acquisition of the second 3D image thus requires a smaller X-ray dose. Typically, a short CT scan is acquired on only a few centimeters of images along the patient's body axis (Z direction). At the extreme, only one slice containing the target area is acquired, but in practice three, five, or much more slices having a width of a few millimeters and separated from each other by a few millimeters are acquired to constitute a local volume in the region of interest that contains the target. Usually, when the region of interest has been determined in the CT imaging device, several acquisitions of the small volume are performed, in order to follow the progression of the instrument when it is progressively inserted. Offering the possibility to navigate the needle with respect to a small volume has the advantage to reduce the number of acquisitions necessary to reach the final target and therefore it reduces the global x-ray dose delivered to the patient and the time of the procedure.

Alternatively, the first and second 3D images are both MR images. Due to the smaller size of the second volume, the acquisition of the second 3D medical image is faster than the acquisition of the first volume.

According to an embodiment, the second volume may be included in the first volume.

Alternatively, at least a part of the second volume extends outside the first volume. This situation may happen if the first volume area had not been set to contain the region of interest.

The second volume may even be completely outside the first volume. This may in particular happen when the first 3D image has been acquired on a region of the patient that is actually at a certain distance of the region of interest. However, as explained below, even if the first 3D image does not correspond to the region of interest, it allows navigating the surgical instrument with respect to the 3D image of the second volume, this second volume including the region of interest (e.g. a target to be treated by the surgical instrument).

The second volume does not include the reference marker in its entirety, i.e. it does not include the reference marker or it includes only a part of the reference marker. Hence, the surgical instrument cannot be navigated with respect to the second 3D medical image directly by means of the reference marker using known navigation techniques.

To overcome this difficulty, the invention proposes to register the second 3D medical image with the first 3D medical image.

Such a registration may be made by any known registration method.

For example, a rough rigid registration may be made based on the DICOM tags of the first and second 3D images. These tags correspond to the position and orientation of the first and second 3D images in a given referential system. Given these information, the first and second 3D images can be rigidly registered.

Figure 2:
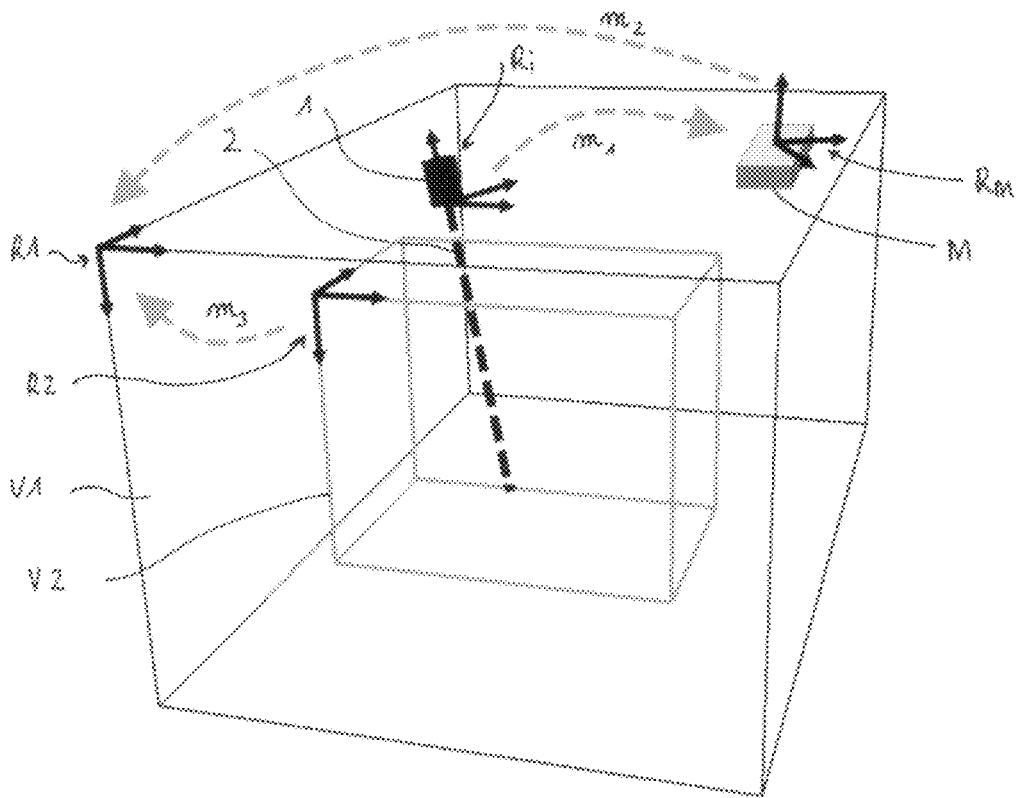
FIG. 2 illustrates the registration of the first and second 3D medical images using a rigid registration technique.

FIG. 2 illustrates schematically such a rough, rigid registration. In this embodiment, the second volume V2 is included in the first volume V1 although, as explained above, this inclusion is not compulsory. A referential system R2 is attached to the 3D image of the second volume V2. A registration based on the DICOM data of the first and second 3D images provides a transformation matrix m3. On the other hand, as already explained with reference to FIG. 1, the position and orientation of the virtual needle 2 with respect to the first 3D image is known by the combination of matrices m1 and m2. Hence, the virtual needle 2 can be navigated with respect to the second 3D image using a combination of matrices m1, m2 and m3.

Typically, each of the DICOM images is a 2D image that contains an index Z that characterizes the translation of the patient along the CT table, which is also the patient's body axis. If the first volume has acquired images from Z1 to Z2, and the second volume has acquired images from Z3 to Z4, and assuming that the patient is a rigid and stable body, a simple translation of the second volume toward the first volume by an amount of (Z3−Z1) will provide the transformation matrix m3. Using the DICOM tags that provide detailed geometric characteristics of the images, it is possible to take into account a difference of tilt of the images with respect to the image table axis, a difference in the image resolution between V1 and V2, and any other geometric difference.

In addition to or in place of such a rough rigid registration, an image to image registration can be carried out. To that end, any image to image registration algorithm known by the skilled person can be implemented. The technique used can for example be a rigid registration between mono-modality images, where only the position and orientation of the first or second volume is modified to match as well as possible the other image. Such algorithms can for example maximize a criteria C1 that can be for example the grey-level voxels correlation of the second image transformed by the searched matrix m4 with the first image in the area where they intersect. Or C1 can be the optimization of entropy criteria, cross-correlation criteria, or any other algorithms that are well known in medical image registration can be applied. It can also be an elastic registration, where not only the position and orientation of the image is modified, but also the image itself, in order to take into account and compensate small motions of the different organs. Another registration technique can be to register the images together using a small region of interest, in which the registration has to be more precise than in the other region of the images. Using a region of interest of the volume V2 instead of the global volume V2 has the advantage to make the process faster and more accurate in the region that is considered and that is usually close to the target. Other registration techniques can be also used, such as deformable models, contour based techniques, etc.

In a particular situation, it is possible that some parts of the fiducials constituting the reference marker are visible and detected in the second image volume V2. When this situation occurs, it is beneficial to use said parts of the reference marker in the image to image registration process. A first method consists in ensuring that the portions of the reference marker are in the region of interest of V2 that is used for image to image registration and then let the algorithm that optimizes the voxels correlation or equivalent proceed. Having high contrasts and rigid structures will help the registration to find a good match. A second method consists in detecting the visible parts of the fiducials in V2 and creating a criterion C2 that represents a distance between said detected fiducials and a model of the same fiducials known by design of the reference marker. Such a criterion C2 can for example a distance between some points characteristics detected on the fiducials and the corresponding points of the model of the reference marker. This criterion C2 is then combined to the image-to-image criterion C1 and a weighted sum of C1 and C2 such as a1 C1+a2 C2, where a1 and a2 can have positive or negative values, is then optimized using conventional algorithms of optimization such as Levenberg-Marquardt algorithm, gradient descents, genetic algorithms or the like. If the value of coefficient a2 is high compared to a1 it will give more importance to the registration of the parts of the fiducials. It is also possible to use the registration of the part of the fiducials as a constraint on some parameters of the image to image registration technique. For example only one point of the fiducials can be used to fix the translation component of the matrix m4 and the rotations components are then determined using the image to image registration.

Figure 3:
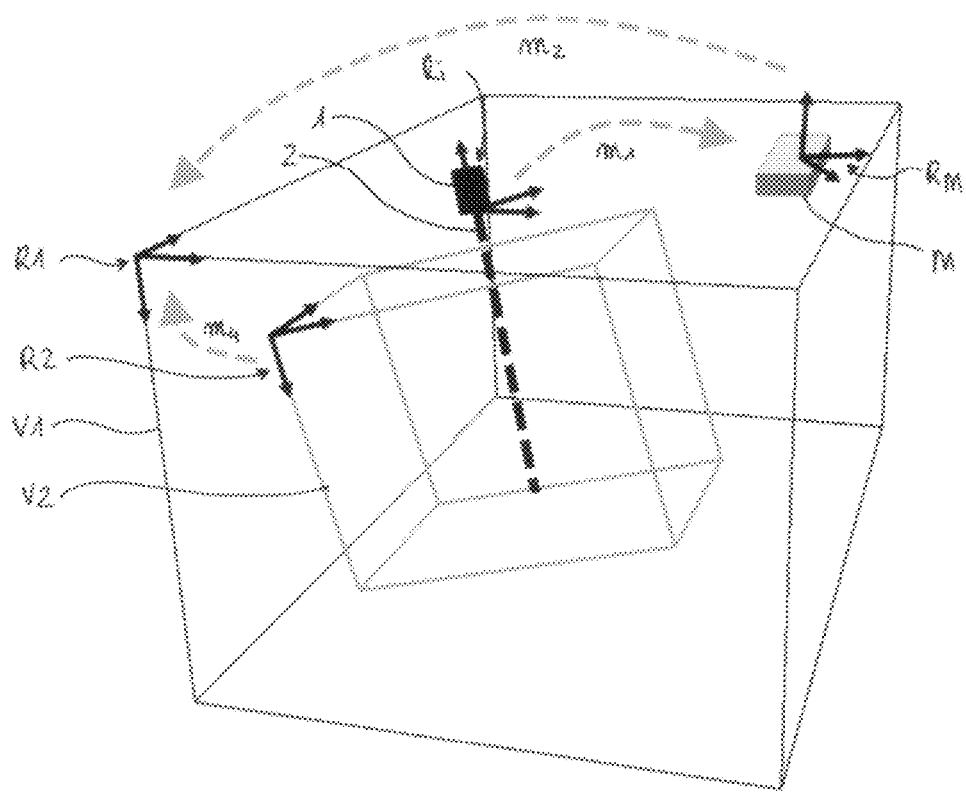
FIG. 3 illustrates the registration of the first and second 3D images using an image to image registration technique.

FIG. 3 illustrates schematically such an image to image registration. In this embodiment, the second volume V2 is included in the first volume V1 although, as explained above, this inclusion is not compulsory. An image to image registration of the first and second 3D images provides a transformation matrix m4. On the other hand, as already explained with reference to FIG. 1, the position and orientation of the virtual needle 2 with respect to the first 3D image is known by the combination of matrices m1 and m2. Hence, the virtual needle 2 can be navigated with respect to the second 3D image using a combination of matrices m1, m2 and m4.

According to an embodiment, the surgical instrument is a needle guide which holds a needle in view of navigating the needle with respect to the second 3D image. In such case, a tracker is attached to the needle guide. Since the needle is slidingly arranged in the needle guide—or fixed to the needle guide—the navigation of the needle guide allows navigating a virtual needle extending along the longitudinal axis of the needle.

If the real needle is partially inserted before the image volume V2 is acquired, the needle can be detected as a trace in the second 3D medical image using known algorithms that detect line segments in 3D images, and the registration may make use of this trace. To that end, the registration may comprise registering said trace of the needle with the virtual position of said needle determined by the tracker attached to the needle guide.

Figure 4:
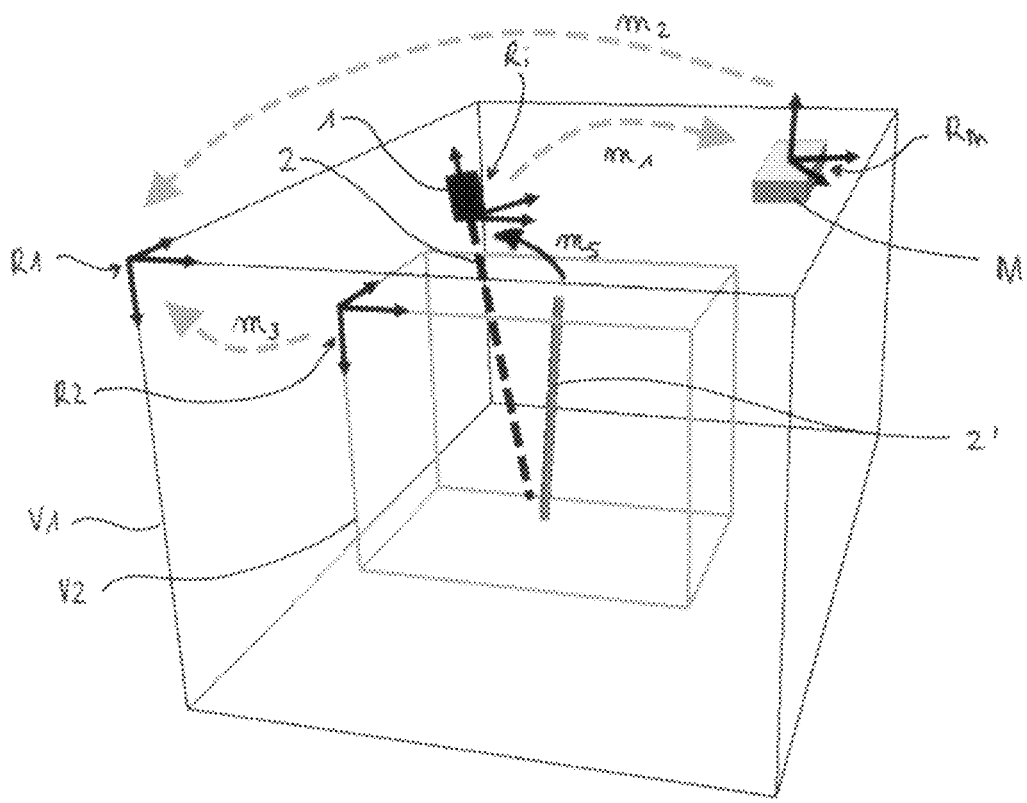
FIG. 4 illustrates the registration of the first and second 3D medical images using a rigid registration technique when a trace of the inserted needle is detected in the second 3D image.

FIG. 4 illustrates the first and second 3D images wherein a trace 2' of the needle can be detected in the second 3D image. As already explained with reference to FIG. 2, the matrix m3 between the referential system R2 of the second 3D image and the referential system R1 of the first 3D image can be determined by a rough, rigid registration of the DICOM tags of both images. The trace 2' of the needle is detected in the second volume by the following procedure. In order to initialize the detection algorithm, the position of the virtual needle in the second volume (which is known by the combination of matrices m1, m2 and m3 as explained above) is used. Having an approximate position to initiate the search for the trace of the needle is useful because it helps the algorithm to find a correct trace of the needle, and if multiple needles are present in the 3D image, it helps to select the one which is considered as the closest from the virtual position when the needle guide is positioned on the needle to be detected. Then, a matrix m5 is computed to register the virtual needle 2 with the trace 2' of the real needle. This registration can be made by any of the techniques described in document WO 2010/086374. For example, one can consider that two degrees of freedom of the matrix m5 are set to zero, the four other degrees of freedom resulting from the registration of the linear shapes of the virtual and real needles. This registration can also benefit from an initialization given by the rough, rigid registration based on the DICOM position and orientation tags.

Alternatively, said two degrees of freedom, which correspond to the translation along and the rotation around the needle axis, can be determined by an image to image registration technique.

Furthermore, said image to image registration technique can be calculated differently in a region of interest (ROI), said ROI being centred on the target to reach, as the registration must be as precise as possible especially in the target region. Thus, a rigid transform can be performed locally, even if the global registration is elastic in order to take into account the motion of the patient and the motion due to the respiratory. This ROI can be centred around a point located on the detected needle axis at a predefined distance from the tip of the detected needle. It can also have a known geometric relationship with the needle guide at an instant determined by the user while navigating the needle guide. For example, the user can point the virtual needle toward the target to indicate that the ROI has to be centred on the tip or on the axis of the virtual needle, at a predefined distance from the tip of the guide.

Figure 5:
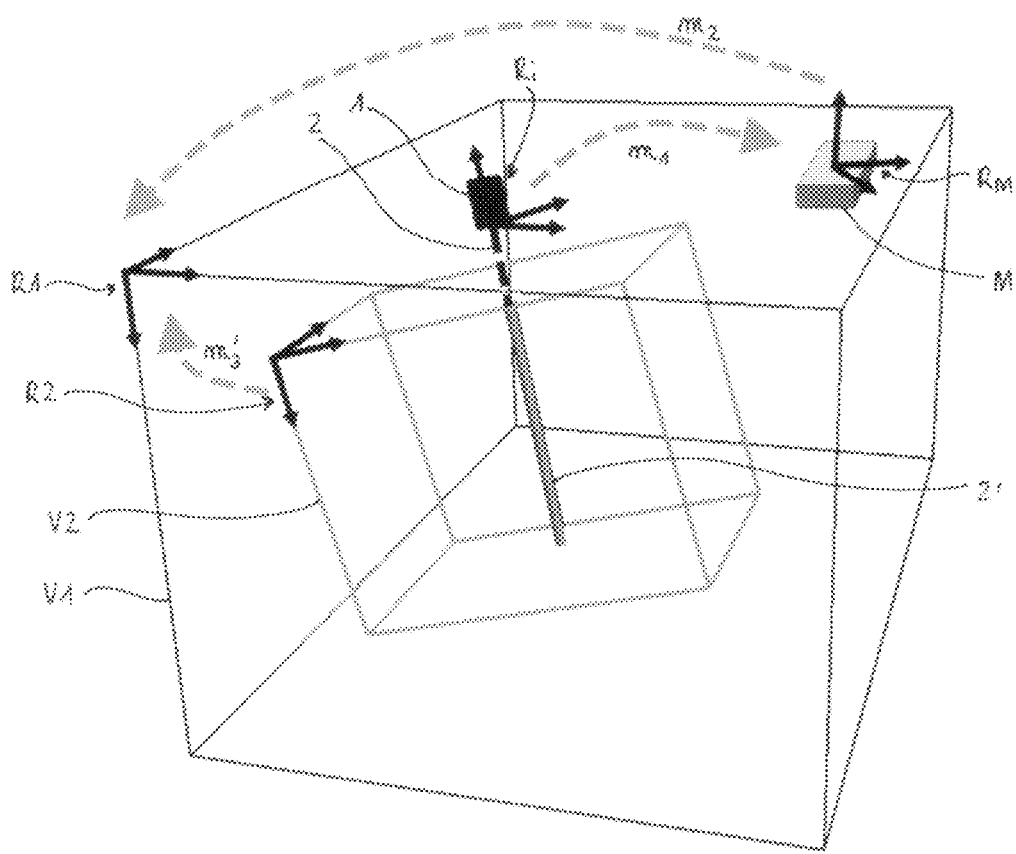
FIG. 5 illustrates the registration of the first and second 3D medical images using an image to image registration technique when a trace of the inserted needle is detected in the second 3D image, said registration comprising registering the virtual needle with the trace of the real needle.

Then, as shown in FIG. 5, the virtual needle can be navigated with respect to the second medical image using a combination of matrices m3' (which results from the combination of matrices m3 and m5 described with reference to FIG. 4), m1 and m2.

Once the registration of the second 3D medical image with the first 3D medical image has been carried out, a virtual position of the surgical instrument with respect to the reference marker can be determined using the tracking system. Then, a processor is able to determine a virtual position of the surgical instrument with respect to the second 3D medical image using the registration matrix.

According to an embodiment, the first 3D medical image—which is generally less recent than the second 3D medical image—can be updated by replacing, in said first 3D medical image, the second volume by the second 3D medical image. Hence, the user benefits from the most recent image in the small volume V2 during the intervention and from the less recent image volume V1 outside of V2. In a preferred embodiment, the image is displayed with full contrast and brightness in V2, and with different visualization parameters, such as a light brown color, or a reduced brightness in the area outside V2 (i.e. V1 less V2).

In a preferred embodiment, if a needle has been partially inserted before V2 has been acquired and a trace of said needle has been detected in the image volume V2 and said trace has been used for registration, then the position and orientation of the virtual needle in the volume V1 is determined using the most recent registration matrix, and not the direct position of the needle guide with respect to the reference marker calculated in the volume V1 in order to benefit from an update that takes into account possible patient motions.

However, this update is not compulsory for the navigation of the surgical instrument and it can be dispensed with, especially when the second volume has a small size.

As explained above, this navigation method allows reducing the X-ray dose and/or acquisition time of the image with respect to which the surgical instrument is navigated.

Another advantage is that the surgical instrument can be navigated with respect to a second 3D image (or a plurality of successive 3D images each corresponding to a different—possibly smaller—volume than the first volume) that is more recent than the first one.

Another advantage of the invention is that, while navigating the surgical instrument with respect to the second 3D image, the user can still benefit from the information provided by the first 3D image which corresponds to a larger volume.

The invention claimed is:

1. A system for navigating a surgical instrument, comprising a processor configured for:
    obtaining a first three-dimensional (3D) medical image of a first volume of a patient's body, said first volume comprising a reference marker attached to the patient's body, the reference marker being configured to be localized by a tracking system,
    registering the first 3D image with said reference marker using fiducials of the reference marker visible in the first 3D image to determine a first transformation matrix,
    obtaining a second 3D medical image of a second volume of the patient's body, said second volume being different from the first volume and not containing all the fiducials of the reference marker, said first and second 3D images being obtained by a single imaging device, the imaging device being distinct from the tracking system,
    registering the second 3D medical image with the first 3D medical image to determine a second transformation matrix,
    obtaining a virtual position of the surgical instrument with respect to the reference marker from the tracking system by determining a third transformation matrix,
    determining a virtual position of the surgical instrument with respect to the second 3D medical image based on the first, second and third transformation matrices.

2. The system of claim 1, wherein the second volume is smaller than the first volume.

3. The system of claim 1, wherein the first 3D image is a volume of Computed Tomography (CT) images of the first volume and the second 3D medical image is a set of CT slices of the second volume, wherein the second volume comprises a target and the first volume is larger than the second volume.

4. The system of claim 1, wherein the first and second 3D images are Magnetic Resonance (MR) images.

5. The system of claim 1, further comprising the surgical instrument, wherein the surgical instrument is a needle guide.

6. The system of claim 5, further comprising a tracker capable of being rigidly attached to the needle guide for navigation of a needle coupled to said needle guide.

7. The system of claim 6, wherein the processor is configured for detecting the needle as a trace in the second 3D medical image and for registering said trace of the needle with the virtual position of said needle.

8. The system of claim 7, wherein the processor is configured for implementing an image to image registration technique to determine, during said registration of the trace of the needle with the virtual position of said needle, a translation along and a rotation about the needle axis.

9. The system of claim 8, wherein the processor is configured for implementing said image to image registration technique in a region of interest having a known geometric relationship with the needle guide or the trace of the needle.

10. The system of claim 1, wherein the second volume is included in the first volume.

11. The system of claim 1, wherein at least a part of the second volume extends outside the first volume.

12. The system of claim 1, wherein the processor is configured for replacing, in the first 3D medical image, the second volume by the second 3D medical image to update the first 3D medical image.

13. The system of claim 1, wherein the processor is configured to implement a rigid registration of the first and second 3D images based on Digital Imaging and Communications in Medicine (DICOM) tags of said images.

14. The system of claim 1, wherein the processor is configured for implementing an image to image registration technique to register the first and second 3D images.

15. The system of claim 14, wherein the processor is further configured for implementing a rigid registration of the first and second 3D images based on DICOM tags of said images and for initializing an iterative computation of the image to image registration technique based on results of the rigid registration based on DICOM tags of said images.

16. The system of claim 14, wherein the surgical instrument is a needle guide and the processor is configured for implementing said image to image registration technique in a region of interest having a known geometric relationship with the needle guide.

17. The system of claim 14, wherein the fiducials of the reference marker are at least partly visible in the second 3D medical image and the processor is configured for implementing said image to image registration technique based on said parts of the fiducials.

18. A method for determining a virtual position of a surgical instrument with respect to a three dimensional (3D) medical image, comprising:
    obtaining a first 3D medical image of a first volume of a patient's body, said first volume comprising a reference marker attached to the patient's body, the reference marker being configured to be localized by a tracking system,
    registering the first 3D medical image with said reference marker using fiducials of the reference marker visible in the first 3D medical image to determine a first transformation matrix,
    obtaining a second 3D medical image of a second volume of the patient's body, said second volume being different from the first volume and not containing all the fiducials of the reference marker, said first and second 3D images being obtained by a single imaging device, the imaging device being distinct from the tracking system, registering the second 3D medical image with the first 3D medical image to determine a second transformation matrix, localizing the surgical instrument with the tracking system, obtaining a virtual position of the surgical instrument with respect to the reference marker from the tracking system by determining a third transformation matrix, determining a virtual position of the surgical instrument with respect to the second 3D medical image based on the first, second and third transformation matrices.

19. The method of claim 18, wherein the second volume is smaller than the first volume.

20. The method of claim 18, wherein the first 3D medical image is a volume of Computed Tomography (CT) images of the first volume and the second 3D medical image is a set of CT slices of the second volume, wherein the second volume comprises a target and the first volume is larger than the second volume.

21. The method of claim 18, wherein the first and second 3D medical images are Magnetic Resonance (MR) images.

22. The method of claim 18, wherein the surgical instrument is a needle guide.

23. The method of claim 22, wherein a tracker is rigidly attached to the needle guide for navigation of a needle coupled to said needle guide.

24. The method of claim 23, wherein the needle is detected as a trace in the second 3D medical image and the registration of the first and second 3D medical images comprises registering said trace of the needle with the virtual position of said needle.

25. The method of claim 24, wherein during said registration of the trace of the needle with the virtual position of said needle, the translation along and the rotation about the needle axis are determined by an image to image registration technique.

26. The method of claim 25, wherein said image to image registration technique is carried out in a region of interest having a known geometric relationship with the needle guide or the trace of the needle.

27. The method of claim 18, wherein the second volume is included in the first volume.

28. The method of claim 18, wherein at least a part of the second volume extends outside the first volume.

29. The method of claim 18, further comprising updating the first 3D medical image by replacing, in said first 3D medical image, the second volume by the second 3D medical image.

30. The method of claim 18, wherein the registration of the first and second 3D images comprises a rigid registration based on Digital Imaging and Communications in Medicine (DICOM) tags of said images.

31. The method of claim 18, wherein the registration of the first and second 3D medical images uses an image to image registration technique.

32. The method of claim 31, wherein the registration of the first and second 3D medical images comprises a rigid registration based on DICOM tags of said images and results of the rigid registration based on DICOM tags of said images are used for initializing an iterative computation of the image to image registration technique.

33. The method of claim 31, wherein the surgical instrument is a needle guide and said image to image registration technique is carried out in a region of interest having a known geometric relationship with the needle guide.

34. The method of claim 31, wherein the fiducials of the reference marker are at least partly visible in the second 3D medical image and said image to image registration technique is carried out using said parts of the fiducials.

* * * * *